United States Patent [19]

Ferrero

[11] Patent Number: 4,684,523

[45] Date of Patent: Aug. 4, 1987

[54] DRAGÉE AND METHOD FOR ITS MANUFACTURE

[75] Inventor: Pietro Ferrero, Brussels, Belgium

[73] Assignee: Ferrero S.p.A., Alba, Italy

[21] Appl. No.: 832,714

[22] PCT Filed: Jun. 14, 1985

[86] PCT No.: PCT/EP85/00284

§ 371 Date: Feb. 14, 1986

§ 102(e) Date: Feb. 14, 1986

[87] PCT Pub. No.: WO86/00226

PCT Pub. Date: Jan. 16, 1986

[30] Foreign Application Priority Data

Jun. 21, 1984 [IT] Italy .............................. 86003 A/84

[51] Int. Cl.$^4$ .......................... A61K 9/36; A23G 3/30
[52] U.S. Cl. ........................................ 424/441; 426/5; 427/3; 424/48; 424/479
[58] Field of Search ................. 427/3; 426/5; 424/16, 424/48

[56] References Cited

U.S. PATENT DOCUMENTS

| 3,982,023 | 9/1976 | Bahoshy et al. | 426/3 |
| 4,168,674 | 9/1979 | Futter | 427/3 |
| 4,238,510 | 12/1980 | Cherukuri et al. | 426/5 |
| 4,317,838 | 3/1982 | Cherukuri et al. | 426/5 |
| 4,562,076 | 12/1985 | Arnold et al. | 426/5 |

FOREIGN PATENT DOCUMENTS

| EP27024 | 4/1981 | European Pat. Off. | 426/5 |
| 3024913 | 9/1981 | Fed. Rep. of Germany. | |

Primary Examiner—Ronald W. Griffin
Attorney, Agent, or Firm—Bernard, Rothwell & Brown

[57] ABSTRACT

The dragée has a core and a shell adhering to the core, based on sorbitol with an additive of the methyl ester of L-aspartyl-L-phenyl-alanine (aspartame) in the proportion of not more than 0.5% by weight. Also described is a tumbling method of making the shell.

9 Claims, No Drawings

DRAGéE AND METHOD FOR ITS MANUFACTURE

The present invention relates to coated edible products, hereinafter called "dragées", comprising a core covered with a shell adhering to the core and in which at least the shell has a sorbitol base. Coated edible products of the kind cited above are typical of the sweet and pharmaceutical industry.

The use of sorbitol as a sweetening constituent agent in the shell and possibly in the core in dragées is known in the art, being particularly desirable for medico-dietetic reasons, and for its weak karyogenic activity.

The disadvantages arising from the high hygroscopicity of sorbitol are also well known, and generally render difficult the tumbling operation carried out in an enrober, which is the basic operation for producing the shell of the dragée. In fact, by carrying out the tumbling operation with aqueous sorbitol-based syrups it proved impossible to obtain a smooth and structurally homogeneous shell. In order to overcome these disadvantages it was proposed, as described in the Italian Patent Application No. 68801-A/79 in the name of the applicant, to use sorbitol including as an additive a small quantity of sucrose esters.

In cases in which the organoleptic characteristics of the dragée are particulary important, as in the case of the sweet industry, the use of sorbitol with small quantities of sucrose ester additives according to known methods, does not, however, prove wholly satisfactory. As is known, in fact, a considerable percentage of consumers do not perceive a very pleasant sensation upon contact of the sorbitol with the palate.

It has now been discovered, and this constitutes the basis of this invention, that this unpleasant sensation on the consumer's palate can be eliminated by adding to the sorbitol a quantity of the methyl ester of L-aspartyl-L-phenyl-alanine in a proportion not greater than 0.5% by weight, while at the same time obtaining a smooth and structurally homogeneous shell.

Therefore one object of the present invention is a dragée comprising a core covered with a shell adhering to the core and in which at least the shell has a sorbitol base characterised in that the shell comprises a plurality of layers consisting essentially of sorbitol and of the methyl ester of L-aspartyl-L-phenyl-alanine (aspartame), the latter being present in a proportion of no more than 0.5% by weight referred to the weight of anhydrous sorbitol.

The methyl ester of the L-aspartyl-L-phenyl-alanine, designated in what follows by the commonly known term aspartame, is a a commercially available synthetic sweetener. Nevertheless its use in the production of dragée has never been suggested up to now. The problems connected with the low solubility of aspartame in water are in fact known, as well as its instability as a sweetener, particularly in aqueous solution, rendering it hardly suitable for use as a constituent of enrobing syrups for tumbling processes.

It has now been discovered that by carrying out the tumbling operation using an aqueous syrup consisting of aspartame and sorbitol, within well-defined concentration limits, it is possible to make dragées with improved organoleptic characteristics and in which the aspartame in the shell retains its sweetening properties for a practically unlimited period.

A further object of this invention is a method for the preparation of a dragée comprising a core and a shell adhering to the core by a tumbling process in an enrober, the said method comprising a plurality of stages of spraying said cores with a sorbitol-based aqueous syrup, characterised in that the said syrup comprises per 100 parts by weight of anhydrous sorbitol, 20 to 60 parts of water and 0.02 to 0.5 parts of aspartame.

As is known the tumbling operation, which will be described in more details below, comprises a plurality of syrup-spraying stages, by means of which the shell is formed in successive layers. Preferably in the method according to the invention, the temperature of the syrup is maintained at 40° to 45° C. in each spraying stage.

It is important that the distribution of the aspartame shall be homogeneous in each single layer formed by sorbitol with aspartame additive. The preferred concentration of the aspartame in the enrobing syrup for the tumbling process referred to the anydrous is 0.05 to 0.3% by weight. The sorbitol utlised in the enrobing syrup must be pure anhydrous sorbitol, free from mannitol, since if mannitol is present the resulting shell has unacceptable hygroscopic characteristics. The enrobing syrup can, however, also contain aromatizers and possibly flavourings, thickeners, colourings or whiteners of known type.

The cores can be formed from various materials, for example almonds, cut liquorice pieces, caramels of various types, gums, gelatines bonbons, or tablets made by pressing various cooked or agglomerate masses. In the case in which the core consists of a food substance sweetened with sorbitol or with a sorbitol base, it is preferable for the sorbitol to have as an additive an aspartame content of not more than 0.5% by weight. It is moreover preferable in these cases for the core to be coated with a thin binding layer for the shell, for example by the deposition upon the core of a solution of stearic acid in alcohol.

EXAMPLE

The example relates to the preparation of a dragée according to the invention in which the core also consists of a food composition including sorbitol. For preparing the core, 2 kg of instantised anhydrous sorbitol were introduced into a mixer. An ethyl alcohol solution of 2% wt. aspartame was prepared and this solution was sprayed into the mixture so as to disperse the aspartame uniformly within the sorbitol. The total quantity of alcohol solution of aspartame utilised was about 100 g, so that the total quantity of aspartame added to the sorbitol was equal to 0.1% by weight of the sorbitol. Mixing continued for a period of about 30 minutes after which the sweetened sorbitol was dried in a fluid bed with air at 35° C. for one hour. The sweetened composition was then re-introduced into the mixer where it was sprayed with an emulsion of flavouring and lubricants in ethyl alcohol. In this phase it is also possible to add to the sorbitol a percentage of thin film xylite up to 40% by weight with reference to the sorbitol in order to render the core more soluble. Following the mixing the substance so produced was introduced into a press to make the cores of the sweets in the form of cylindrical pallets with rounded edges having a diameter of 5 mm and a length of 11 mm. The cores thus made were coated with an alcohol solution of up 25% of stearic acid in ethyl alcohol using a quantity of this solution equal to 0.2% of the weight of the sorbitol composition.

A syrup for the tumbling process is prepared to one side, formed by 100 parts by weight of pure anhydrous sorbitol free from mannitol, 33 parts by weight of water 0.25 parts by weight of aspartame and 1 part flavourings. Preparation of the syrup was carried out by the addition of the aspartame to water at a temperature betwee 40° and 45° C. while stirring, until complete dissolution. The sorbitol and flavourings were then introduced into the solution thus produced. For the tumbling operation an enrobing pan 45 cm diameter was used, rotating about an axis inclined at 30° to the vertical, at a speed of 47 revolutions per minute. The cores made by the procedure described above were introduced into the pan. The tumbling process was carried out in 60 cycles and consisted of the following stages:

(a) spraying for 10 seconds with 45 g of syrup at a temperature of 40° to 45° C.;
(b) a pause for homogenisation for about 30 seconds;
(c) dusting for 5 seconds with about 4–5 g of sorbitol film;
(d) a pause for homogenisation for another 30 seconds;
(e) drying with air at a temperature of about 45°±10° C. for about 3±1 minutes;

The aforesaid stages were repeated until a typical final weight equal to about twice the initial weight of each core was reached. The weight of the finished product therefore amounted to about 4 Kg. No difficulties whatever were encountered in the tumbling process. The individual dragées had a white firm shell with no roughness. It is noted that by using the process according to the invention it is possible to produce a shell having the desired characteristics even in the absence from the entobing syrup of the sucrose esters suggested by known methods.

Tasting tests were moreover carried by placing before a jury of 10 tasters a portion of sweets freshly made by the above descrbed method, and a portion made by the same method and kept for a period of three months at ambient temperature. None of the tasters was able to perceive the albeit minimal difference between the products of the two portions, thus confirming the stability of the aspartame sweetener in the sweet product.

I claim:

1. A dragée comprising a core covered by a shell adhering to the core, said shell being obtained by spraying a sorbitol-based aqueous syrup on said core while tumbling said core in an enrober, characterized in that the shell comprises a plurality of layers consisting essentially of sorbitol and of the methyl ester of L-aspartyl-L-phenyl-alanine (aspartame), the latter being present in a proportion of no more than 0.02 to 0.3% by weight of anhydrous sorbitol in said shell.

2. A dragée according to claim 1 in which the core consists of a food composition including, sorbitol, characterized in that the sorbitol in the core has as an additive an aspartame content not greater than 0.5% by weight of the anhydrous sorbitol.

3. A dragée according to claim 2, characterized in that it includes a binding layer interposed between the shell and the core and including stearic acid.

4. A dragée according to claim 1, wherein said layers further comprise one or more additives selected from the group consisting of aromatizers, flavourings, thickeners, colourings and whitenings.

5. Method for the preparation of a dragée comprising a core and a shell adhering to the core, by tumbling in an enrober, the said method incuding a plurality of stages of spraying said cores with a sorbitol-based aqueous syrup characterized in that said syrup consists essentially of anhydrous sorbitol, from 20 to 60 parts of water, and 0.02 to 0.3 parts of aspartame referred to 100 parts by weight of said anhydrous sorbitol.

6. Method according to claim 5, characterised in that during the operation of spraying with the enrobing syrup, the syrup is maintained at a temperature of 40° to 45° C.

7. Method according to claim 5, wherein said syrup further comprises one or more additives consisting of aromatizers, flavourings, thickners, colourings and whitenings.

8. Method according to any of claims 5 wherein prior to the tumbling in the enrober said cores are coated with an alcohol solution of stearic acid.

9. A dragée comprising a core, the core being tumble-enrobed by a shell sprayed onto the core and adhering to and covering the core, said shell being obtained by spraying a sorbitol-based aqueous syrup on said core while tumbling said core in an enrober, characterized it that the shell comprises a plurality of layers of a substantially mannitol-free mixture consisting essentially of sorbitol and of the methyl ester of L-aspartyl-L-phenyl-alanine (aspartame), the latter being present in a proportion of no more than 0.02 to 0.3% by weight of anhydrous sorbitol in said shell.

* * * * *